(12) United States Patent
Hettiarachchy (10) Patent No.: US 9,894,920 B2
(45) Date of Patent: Feb. 20, 2018

(54) YEAST FERMENTATION OF RICE BRAN EXTRACTS

(71) Applicant: Board of Trustees of the University of Arkansas, Little Rock, AR (US)

(72) Inventor: Navam Hettiarachchy, Fayetteville, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 481 days.

(21) Appl. No.: 14/796,458

(22) Filed: Jul. 10, 2015

(65) Prior Publication Data

US 2015/0305374 A1 Oct. 29, 2015

Related U.S. Application Data

(62) Division of application No. 11/887,724, filed as application No. PCT/US2006/011625 on Mar. 30, 2006, now Pat. No. 9,179,687.

(60) Provisional application No. 60/666,673, filed on Mar. 30, 2005.

(51) Int. Cl.
| | |
|---|---|
| A23L 1/105 | (2006.01) |
| A23C 9/13 | (2006.01) |
| A23C 9/133 | (2006.01) |
| A23L 7/10 | (2016.01) |
| A23L 7/104 | (2016.01) |
| A61K 36/899 | (2006.01) |

(52) U.S. Cl.
CPC .............. *A23L 1/105* (2013.01); *A23C 9/133* (2013.01); *A23C 9/1307* (2013.01); *A23L 7/104* (2016.08); *A23L 7/115* (2016.08); *A61K 36/899* (2013.01)

(58) Field of Classification Search
CPC ....... A23C 9/1307; A23C 9/133; A23L 1/105; A23L 1/1016; A23L 7/104; A23L 7/115; A61K 36/899
See application file for complete search history.

(56) References Cited

U.S. PATENT DOCUMENTS

| | | | |
|---|---|---|---|
| 4,358,462 | A | 11/1982 | Takeda |
| 5,118,503 | A | 6/1992 | Sawai et al. |
| 5,776,756 | A | 7/1998 | Kimura et al. |
| 6,303,586 | B1 | 6/2001 | McPeak et al. |
| 6,368,835 | B1 | 4/2002 | Saitoh et al. |
| 2001/0019734 | A1 | 9/2001 | Gilbertson et al. |
| 2009/0035399 | A1 | 2/2009 | Hettiarachchy |

OTHER PUBLICATIONS

Birol, G, et al "Ethanol production and fermentation characteristics of recombinant *Saccharomyces cerevisiae* strains grown on starch" Enzyme and Microbial Technology 22:672-677, 1998 (Year: 1998).*

Lima et al.: The Functioinal Effectiveness of Reprocessed Rice Bran as an Ingredient in Bakery Products; Nahrung/Food 46 (2002) No. 2, pp. 112-117.
AACC, 1990, Approved Methods of the American Association of Cereal chemists, 8th ed., vol. 2, AACC, St. Paul, Minn. Nos. 32-21, 46-08, 76-11.
Ames, B., et al., "Method for detecting carcinogens and mutagens with *Salmonella*/mammalian microsomes mutagenicity test," Mutat. Resch. 1975, 31:347-364.
AOAC Method 982.30a, 1990, in Official Methods of Analysis, 15th Edition. Association of Official Analytical Chemists, Arlington, Va., pp. 1096-1097.
Cai, R., et al., High-perfonnance liquid chromatography detennination of phenolic constituents in 17 varieties of cowpeas, J Agric Food Chem. 2003,51:1623-1627.
Gibson, G., et al., "Dietary modulation of the human colonic microbiota: introducing the concept of prebiotics," J. Nutrition, 1995, 25: 140 1-1412.
Hettiarachchy, N., et al., "Natural Antioxidant Extract from Fenugreek (Trigonella foenumgraecum) for Ground Beef Patties," 1. Food Sci~ 1996a, 61(3):516-519.
Hettiarachchy, N., et al., "Preparation and Functional Properties of a Protein Isolate from Defatted Wheat Germ, " Cereal Chem., 1996b, 73(3 ):363-367.
White P., et al., "Antioxidants from Cereal and Legumes," in Natural antioxidants: chemistry, health effects and applications. AOCS Press, Champaign, Ill., Shahidi, F., ed., 1997, pp. 25-63.
Maron, D., et al., "Revised methods for *Salmonella* mutagenicity test," Mutat. Resch., 1983, 113:173-215.
Rowland, I. et al., "Probiotics and benefits to human health," Envir. Microbio., 1999, 1(5),375-382.
Singleton V., et al., "Colorimetry of total phenolics with phosphomolybdic-phosphotungstic acid reagents," Am. J. Enol. Vitic., 1965, 16: 144-158.
Tang, S., et al., "Protein extraction from heat-stabilized defatted rice bran. 1. Physical processing and enzyme treatments," 1. Agric. Food Chem., 2002,50:7444-7448.
Tang, S., et al., "Protein extraction from heat stabilized defatted rice bran. n. The role of amylase, celluclast, and viscoyme," J. Food Sci.. 2003a, 68(2):471-475.
Tang, S., et al., "Physicochemical properties and functionality of rice bran protein hydrolyzates prepared from heat-stabilized defatted rice bran with the aid of enzymes," J. Food Sci., 2003b, 68(1):152-157.
Wang, M., et al., "Preparation and functional properties of rice bran protein isolate (from non-heat treated defatted rice bran)," J. Agric. Food Chem., 1999, 47(2):411-416.

(Continued)

*Primary Examiner* — Christopher R Tate
*Assistant Examiner* — Aaron J Kosar
(74) *Attorney, Agent, or Firm* — Crowe & Dunlevy, P.C.

(57) ABSTRACT

Heat-stabilized defatted rice bran (HDRB) is fermented with yeast to afford a food product having superior prebiotic for probiotic properties. Fermentation of HDRB with yeast yields a prebiotic composition that can promote the growth and/or activity of beneficial intestinal bacteria (probiotic) when consumed by an animal or human. The prebiotic and/or probiotic compositions can afford substances having desirable health effects when consumed. The yeast fermented, and the probiotic fermented extracts and residues will have several nutraceutical compounds including protein, phenolics, phytic acid, arabinose, bioactive isoflavones, dietary fibers and several others that will have health benefits. Inclusion of legumes during fermentation can synergistically enhance the bioactivities of HDRB. HDRB can be a source of growth medium for yeast/mold/microorganisms.

13 Claims, 2 Drawing Sheets

(56) References Cited

OTHER PUBLICATIONS

P. J. Coote, M. V. Jones, I. J. Seymour, D. L. Rowe, D. P. Ferdinando, A. J. McArthur and M. B. Cole, Activity of the plasma membrane H+-ATPase is a key physiological determinant of thermotolerance in *Saccharomyces cerevisiae*, Microbiology (1994), 140, 1881-1890.

Singh, B., et al., Suitability of Full Fat and Defatted Rice Bran Obtained from Indian Rice for Use in Food Products, Plant Foods for Human Nutrition, 47: 191-200, 1995.

* cited by examiner

YEAST FERMENTATION OF RICE BRAN EXTRACTS

CROSS-REFERENCE TO RELATED APPLICATIONS

This application claims priority to and is a divisional of U.S. patent application Ser. No. 11/887,724, filed Sep. 29, 2007, which is a national stage filing under 35 U.S.C. §371 of International Application PCT/US2006/011625, filed Mar. 30, 2006, which claims the benefit of U.S. Provisional Patent Application No. 60/666,673, filed Mar. 30, 2005, each of which is incorporated herein by reference in its entirety.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

REFERENCE TO A SEQUENCE LISTING, A TABLE, OR A COMPUTER PROGRAM LISTING APPENDIX

Not Applicable.

STATEMENT REGARDING PRIOR DISCLOSURES BY THE INVENTOR OR A JOINT INVENTOR

Not Applicable.

BACKGROUND OF THE INVENTION

1. Field of the Invention

This invention relates to fermented rice bran extracts and the resulting compounds.

2. Description of the Related Art

Rice bran forms 8-10% of the total weight of rough rice and contains approximately 90% of its nutrients and nutraceuticals. This makes rice bran a prime candidate for processing that increases the production of its valuable components. The U.S. food industry can remain competitive in a global economy by developing, from inexpensive and underutilized resources, value-added functional foods/ingredients having health benefits and consumer acceptability. The nutraceutical and functional food industry has evolved into a market worth $20.2 billion in 2002. It is estimated that the functional food industry in the U.S. could double in value by 2007 [Market Research, 2002].

Commercially, rice bran is stabilized by heat treatment to prevent deterioration resulting from hydrolysis and oxidation of oil. The commercial rice bran product after heat treatment and removal of oil (15-20%) is referred to herein as heat-stabilized, defatted rice bran" (HDRB), and is mainly used for animal feed and pet foods. Heat treatment results in protein denaturation and aggregation with other components, and lowers protein and phytochemical extractability. HDRB contains approximately 10.5-12.0% water, 18.5-20.9% protein, 1.5-2.0% lipid, 15.3-16.8% starch, 25.2-25.6% total fiber, 2.0-2.5% total phenolics, 1.73-2.28% phytic acid, and 9.0-10.4% ash [Hettiarachchy, 2003]. In addition, rice bran contains B-vitamins and minerals, and trace elements. The positive nutritional and nutraceutical attributes of rice bran include hypoallergenicity, gluten-free, and a source of dietary fiber.

Prebiotic. The term "prebiotic" is used to refer to a "non-digestible food ingredient that beneficially affects the host by selectively stimulating the growth and/or activity of one or a limited number of bacteria in the colon, and thus improves host health" [Gibson, et al.]. Resident gut microflora ferment prebiotics, mainly provided in the diet, which generally cannot be digested by the host in the upper part of the digestive tract. These include non-starch polysaccharides (dietary fiber), oligosaccharides, oligopeptides, etc. The resistant oligo products in the digestive tract can be utilized as substrates for the growth and/or activity of beneficial bacteria, e.g., *Bifidobacterium* spp. and *Lactobacillus* spp.

Probiotic/Synbiotic. A "probiotic" is a live microbial organism that is beneficial to health. The combination of a probiotic and a prebiotic is called a "synbiotic". The interaction of probiotics and prebiotics (synbiotics) has not been researched in detail. Prebiotics ensure the survivability of some beneficial bacteria, especially *Bifidus* bacteria. Synbiotics are generally more stable because a true pro biotic, in the absence of a prebiotic, is often not very viable. Without a specific synbiotic food source, a probiotic has to deal with a greater propensity for oxygen intolerance, low pH intolerance and temperature intolerance. Also, it is believed that the beneficial activity of probiotics requires specific prebiotic substrates for effective performance.

Exemplary food grade and generally regarded as safe (GRAS) probiotics include *Lactobacilli* (*Lactobacillus acidophilus, L. casei, L. delbrueckii* subsp *bulgaris, L. brevis, L. cellobiosus, L. curvatus, L. fermentum, L. plantarum, L. gasseri, L. rhamnosus*), Gram positive cocci (*Lactococcus lactis* subsp *cremoris, Streptococcus salivarius* subsp *thermophillus, Enterococcus faecium, S. diacetylactis, S. intermedius*), Bifidobacteria (*Bifidobacterium bifidum, B. adolescentis, B. animalis, B. in/antis, B. longum* and *B. thermophilum*) and Yeasts (*Saccharomyces boulardi, S. cerevisiae* and other strains). This also includes the genetically modified recombinant strains of *S. cerevisiae* (ATCC 13007, YPB-G, ATCC 4126, YPG/AB, YPG/MM, ATCC 201160), which have potential protease and carbohydrase, esterase activities.

Probiotic bifidobacteria plays an important role in human health as indicated by suppression of liver tumorigenesis in mice [Mitzutani, et al.], cholesterol reduction [Moleder, et al.], improvement of lactose utilization in malabsorbers [Jiang, et al.], deconjugation of bile acids [Lankaputhra, et al.] and increasing immunity in host animals [Simone, et al.]. Consumption of foodstuffs that promote the growth and/or activity of intestinal Bifidobacteria accordingly can enhance the health of the host.

Studies in several experimental models have shown consistently that synbiotics added to the diet of animals can dramatically reduce the development of cancer. Synbiotic combinations reportedly are more potent than either their prebiotic or probiotic components when tested alone [Rowland, et al.].

Bioactive Anti-Angiogenic Proteins. Many well-established bioactive proteins have demonstrated anti-angiogenic activity and cholesterol-lowering effects [S. Li, et al.]. Reported anti-angiogenic bioactive proteins include protamine [Y. Li, et al.], the Bowman-Birk inhibitor (BBI) from rice, soybean and legumes [Kennedy], lactoferrin [Norrby, et al.], and lysozyme [Yamamoto, et al.].

Bioactive anti-mutagen compounds. Naturally occurring anti-mutagens and anti-carcinogens have been reported in fresh fruits and vegetables, and fermented food [Karakaya, et al.]. Glycoproteins purified from a culture supernatant of lactic acid bacteria (LAB) showed strong antimutagenicity [Rhee, et al.].

Bioactive anti-microbial compounds. Food-borne pathogens are a great concern to consumers and cause significant annual losses to the food industry. *L. monocytogenes, S. typhymurium* and *E. coli* 0157:H7 are among the most important pathogens that have caused a significant number of outbreaks. Frequent outbreaks demonstrate a need for development of intervention strategies using antimicrobial agents to ensure the microbial safety of food.

Bioactive antioxidant compounds. Antioxidants are used in a wide variety of food products including lipids, lipid-containing foods, and packaging materials [Madhavi, et al.]. Several plant extracts have demonstrated antioxidant activities. An extract of rosemary leaves exhibited the most effective antioxidant activity among the herbs evaluated for this quality [Chang, et al.]. Cereals and legumes are rich sources of antioxidant compounds, such as phenols and derivatives, and tocols. Alpha tocopherol is the most abundant tocol in food and also the most biologically active compound [White, et al.]. However, tocopherols also have pro-oxidant effects, which limit their use in product applications. The flavor and color in plant antioxidant extracts contribute to limited usage. Antioxidant activities have been demonstrated in cereal, plant, and fenugreek extracts [Onyeneho, et al. 1991, 1993; Hettiarachchy, et al. 1996a].

Much research has been conducted on the preparation, purification, identification, and characterization of proteins from rice bran using enzymes [Hettiarachchy, et al., 1996b; Tang, 2002, Tang et al., 2002; Tang et al., 2003a, 2003b; Wang, et al.]. The nutraceutical properties and functional uses of rice bran protein for several food and pharmaceutical applications are being studied. Polyphenolic extracts and their constituents derived from selected plant materials are under investigation for antioxidant, antimicrobial, and anti-mutagenic activities [Cai, et al.].

U.S. Pat. No. 5,118,503 (issued to Sawai, et al.) proposes a composition obtained from rice bran that comprises a filtrate of lactic fermented and aged material of the rice bran. U.S. Pat. No. 5,776,756 (issued to Kimura, et al.) proposes fermentation compositions made from rice brans and soybeans, which have superoxide dismutase and antihypertensive activities. The fermentation composition is prepared using *Bacillus* microorganisms. U.S. Pat. No. 4,358,462 (issued to Takeda) proposes a method of producing an alcoholic beverage from rice that includes fermentation of a saccharified rice mash or slurry with yeast. The saccharified mash or slurry is formed by saccharifying cooked or steamed rice with an enzyme composition containing a saccharifying enzyme produced by *Rhizopus, Aspergillus, Endomyces* or *Bacillus subtilis* microorganisms.

Yeast, a unicellular eukaryotic microorganism, is used in baking, brewing, wine making, and biotechnology and is the most intensively studied organism for many biological and biochemical aspects. Many types of yeast are generally regarded as safe to human beings, which give them advantages for application in food compared to other organisms. Yeast cells have advantages for experimentation and application because of a much higher metabolic rate, a more rapid growth rate, and consequently the ability to bring about chemical changes very quickly.

It is an objective of the present invention to produce food grade yeasts or microorganisms using rice bran as an economical substrate medium. It is also an objective of the present invention to release the bound protein, phenolics and other phytochemicals from rice bran using the enzymes produced during fermentation. In rice bran more than 70% of the phenolics are in the insoluble bound form, in which they are cross-linked to carbohydrates in the cell matrix and thus are difficult to extract. Another objective of the present invention is to enhance the prebiotic and/or probiotic utilities of rice bran using yeast fermentation and probiotic processes. A further object of the present invention is to develop and identify novel nutraceuticals and health beneficial ingredients derived from rice bran by yeast, mold, microorganism and pro biotic fermentations, which should increase the economic value of this commodity.

BRIEF SUMMARY OF THE INVENTION

The present invention pertains to fermentation of rice bran with one or more strains of yeast. It has now been discovered that the yeast produces enzymes effective in releasing proteins, phenolics, phytic acid, and other chemical compounds present in the rice bran. The rice bran is typically a heat-stabilized product and can be defatted. It is found that the yeast-fermented rice bran is an effective growth medium for yeast, mold, and microorganisms, and that the soluble extract left after yeast growth can be an effective prebiotic for probiotics when consumed by an animal or human.

A prebiotic of the present invention selectively promotes the growth and/or activity of beneficial intestinal bacteria. A composition of the present invention comprising prebiotics and/or probiotics can be effective in preventing, inhibiting or ameliorating an adverse health condition of a human or animal. Specifically, the HDRB extract derived after the growth of yeast and other probiotics can be effective, when administered to the human or animal, as an anti-mutagenic, antioxidant, anti-hyperglycemic, anti-hypercholesterolemic, and/or anti-inflammatory agent, and can also inhibit urogenital or gastrointestinal tract infections, and promote gut motility. Inclusion of legumes during fermentation can synergistically enhance the bioactivities of HDRB.

DETAIL DESCRIPTION OF THE INVENTION

The present invention is directed to utilizing rice bran, preferably heat-stabilized defatted rice bran (HDRB), as a source to produce yeast and other microorganisms, as well as for assessing the ability of yeast/mold/microorganisms fermentation to release functional and health beneficial ingredients from rice bran. When yeast, mold or microorganisms are grown in HDRB medium, extracellular enzymes, including amylases, cellulases, xylanase, esterases, and proteases, secreted by the yeast/mold/microbes can convert the complex components of the rice bran into simpler molecules. By controlling the conditions of yeast/mold/microbial growth in HDRB, suitable prebiotics containing oligo components (indigestible oligosaccharides, resistant starch, oligopeptides, etc. that can be effectively used by probiotics) can be produced that serve as sources of energy and nitrogen for intestinal probiotics, including *Bifidobacterium* spp. and *Lactobacillus* spp. The probiotics can also release phenolics and other phytochemicals from yeast-treated (also, mold/microorganism-treated) HDRB to provide a variety of health benefits, e.g., anti-mutagenic, antioxidant, and antimicrobial activities. Additionally, yeast/mold/microbial-cultured HDRB can produce combined prebiotic and probiotic (synbiotic) formulations that have beneficial health effect. These beneficial substances can be incorporated into human or animal diets as nutraceuticals or functional food ingredients.

Accordingly, a first aspect of the present invention is directed to methods of producing yeast, as well as the resulting compositions, which utilize HDRB as a principal growth medium. Preferably, the rice bran is defatted. Commercial sources of the rice bran, either defatted or not, are available from Riceland Foods Inc.; Stuttgart, Ark. or other suppliers who mill rough rice. Preferred yeast strains for conducting the fermentation include *Saccharomyces cerevisiae* (ATCC26603, ATCC 58527, ATCC 7754) and *Saccharomyces fibuligera* (ATCC 9947) or *Bacillus* strains or specific recombinant strains of *Saccharomyces cerevisiae*, such as ATCC 4126, YPG/MM, and YPB-G. (ATCC= American Tissue Culture Collection; Manassas, Va.). The HDRB suspension can be sonicated prior to fermentation. Sonication uses ultrasound waves to disrupt the cell wall structure and adjacent carbohydrate matrix, which increases the surface area of the exposure of cellular fragments to enhance the efficiency of catalysis of enzymes secreted by yeast/mold/microorganisms. Also contemplated is a method for using HDRB as a growth medium for non-yeast microorganisms, e.g., mold and bacteria.

In another aspect of the invention, a composition of matter comprises yeast-fermented, heat-stabilized rice bran. Exemplary solvents include water or water-based solution. Preferably, the solvent for fermentation is water. The selected solvent should not diminish the bioavailability, shelf life or efficacy of the yeast-fermenting HDRB. It is preferred that the yeast/mold/microorganism-fermented HDRB is an effective pre biotic when consumed by an animal or human. It can be a source of dietary fiber or a dietary food supplement. It is additionally, or alternatively, preferred that the yeast and yeast-fermented HDRB selectively promotes growth and/or activity of beneficial intestinal bacteria (probiotic) when consumed by an animal or human. Such efficacy can be demonstrated in an in-vitro system, such as by laboratory studies of cultures of *Bifidobacterium infantis, Bifidobacterium longum, Bifidobacterium bifidum*, and *Bifidobacterium adolescentis*. Notably, a composition of the present invention can be subjected to fermentation by Bifidobacteria, either in vivo or in vitro.

Also contemplated is a method of making a yeast/mold/microorganism fermented rice bran product. Such method comprises grinding the rice bran to a fine particulate mass, combining the particulate mass with water to form a liquid suspension and autoclaving, fermenting the suspension for at least twelve hours, centrifuging the fermented suspension, removing a supernatant layer, separating insoluble residue from the remaining liquid, and drying the remaining liquid to a powder. The fermented product can also be dried without separating the insolubles and used as an ingredient.

Human or animal consumption of a composition of the present invention preferably has a beneficial effect on the consumer's health, due to the composition's prebiotic and/or probiotic activities. Physical forms of the composition for administration include pill, lozenge, spray, suppository, powder, solution, suspension, or dietary supplement form, and the like. A composition can also include a legume or cereal component, such as soy meal or soy protein isolate. The soy meal or soy protein can itself be a source of bioactive components having functional and nutraceutical properties. Also soy meal or soy protein can be combined with HDRB and fermented with yeast/mold/microbes/probiotics for synergistic nutraceutical effect and health benefits. As an example, isoflavones in soy beans are present in inactive aglycone forms. These aglycones have no health benefits; however, they can be converted to glycones for nutraceutical effect. During fermentation, enzymes secreted by the yeast/fungi/microorganisms can convert the inactive glycones to aglycones that have health benefits. Examples of isoflavone conversions are genistin to genestein and daizin to diadzein.

Accordingly, in a further aspect, a composition of the invention is effective in preventing, inhibiting or ameliorating an adverse health condition of a human or animal by administering a probiotic yeast-fermented, heat-stabilized rice bran composition to the subject. For example, a composition is effective in mediating or affecting inhibition of pathogenic microbial growth, production of anti-mutagenic substances, production of antioxidant substances, production of anti-hyperglycemic substances, production of anti-inflammatory substances, and/or production of anti-hypercholesterolemic substances, inhibition of urogenital and gastrointestinal tract infections, promotion of gut motility, and prevention of heart disease. Therefore, specific disease conditions addressed by the composition include pathogenic intestinal bacterial growth, cancer, urogenital and gastrointestinal tract infections, gut motility, heart disease, hyperglycemia, inflammation, and hypercholesterolemia.

Additional aspects of the invention comprise quantifying major components in heat-stabilized defatted rice bran (HDRB) that can be substrates for yeast/mold/microbial growth, and evaluating HDRB as a yeast growth medium (for example, *S. cerevisiae*/mold/microorganisms). Yeast can be cultured under controlled conditions to partially digest complex compounds in HDRB. The partially digested extract can be used as a growth medium for beneficial intestinal organisms, including selected species of *Bifidobacterium* and *Lactobacillus*, and other related food grade species that can generate bioactive compounds.

Another aspect of the present invention entails an in-vitro synbiotic system comprising a yeast/mold/microbecultured HDRB extract (prebiotic) and at least one strain of *Bifidobacterium* spp and *Lactobacillus* spp (probiotic) or any other food grade suitable probiotic. Selection of the strain is based on the type(s) of probiotic species that demonstrate optimum growth in the partially digested HDRB by yeast. More than one probiotic in combination can be used for synergism.

Synbiotics-HDRB compositions that demonstrate superior performance can be incorporated into yoghurt, beverage milk products and infant formulates as a life supplement of probiotics. The probiotics and synbiotics that demonstrate superior performance in stability and growth in yoghurt and dairy beverage can be selected and sensory evaluation and consumer acceptability on products stored at 4° C. for 0, 14 and 28 days can be conducted. Yeast-cultured HDRB and probiotic grown yeast/mold/microorganism-cultured HDRB extracts can be evaluated for antioxidant, antimicrobial, anti-mutagenic, anti-inflammatory, and anti-hyperglycemic effects.

Furthermore, HDRB is a rich medium for the growth of a range of fungi and microorganisms. The yeast treated HDRB or the HDRB can be subjected to food grade fungi or microorganisms that produce enzymes, which release bound phenolics and proteins. Such organisms include *Bacillus pumilus* (ATCC 7061), *Bacillus subtilis* (ATCC 6051 NRRL NRS-74), and several other food grade bacilli. The phenolics, arabinose and proteins released are valuable compounds that have nutraceutical and health benefits. The rice bran protein has a superior amino acid composition in comparison to other cereal proteins, and is hypoallergenic. This protein can find use in a variety of health products.

The invention is now described with reference to certain examples for purposes of clarity and illustration, but not by way of limitation.

EXAMPLES

Example 1

Growth Performance of Yeast (*Saccharomyces cerevisiae*) in Heat-Stabilized Defatted Rice Bran (HDRB)

Figure 1:
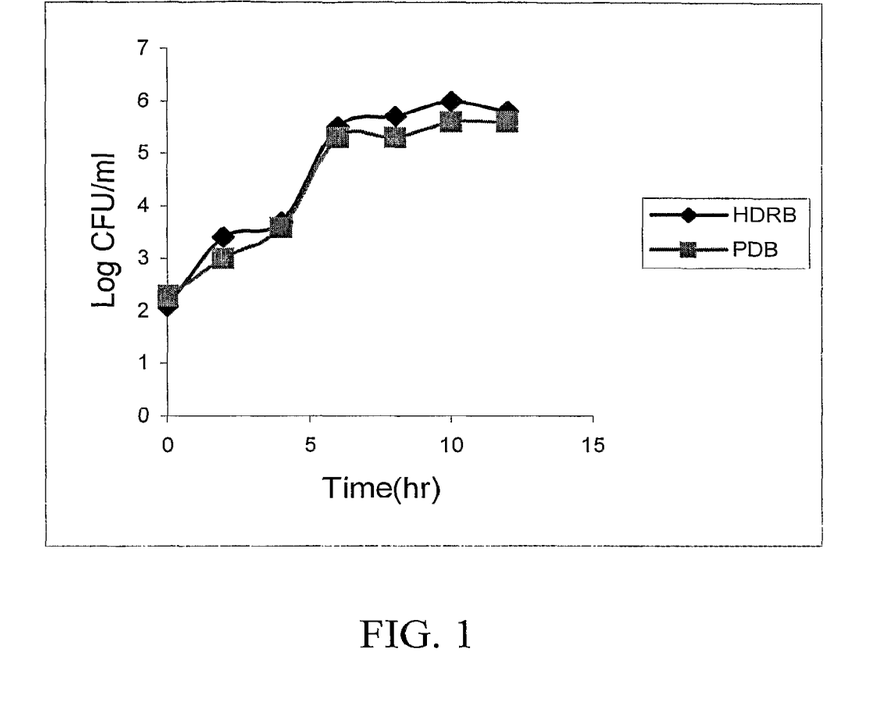
FIG. 1 shows growth performance of yeast (*S. cerevisiae*) in potato dextrose broth (PDB) and heat-stabilized defatted rice bran (HDRB) medium. Maximum growth was observed under the following conditions: 4.8 g HDRB/200 mL medium, 5% w/v yeast, and 10-12 h incubation time. A similar growth performance of yeast in HDRB as in PDB (standard medium) was observed under the same conditions.
Figure 2:
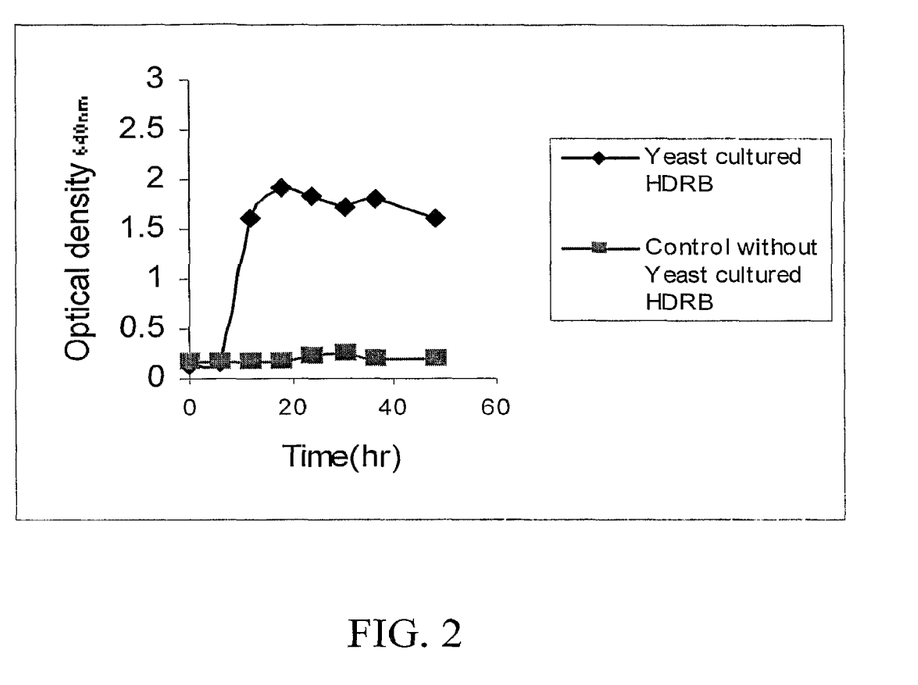
FIG. 2 shows growth performance of *Bifidobacterium bifidum* (NCFB 1454) in yeast-cultured HDRB. Maximum growth was observed at about 20 hours at 37° C., anaerobically. One concentration of yeast-cultured HDRB was studied to assess the feasibility of using this extract as prebiotic for one strain, i.e., *Bifidobacterium bifidum*.

Yeast (*Saccharomyces* strain ATCC 26603) was grown in sterilized PDB/HDRB: 4.8 g/200 ml. Incubation was at 30° C. and shaking was at 200 rpm. Colonies were enumerated on a potato dextrose agar (PDA) plate. The results are shown in FIG. 1. Maximum growth was observed at 5% w/v yeast and 10-12 h incubation time. A similar growth performance of yeast in HDRB and PDB (standard medium) was observed under the same conditions.

Example 2

Growth Performance of *Bifidobacterium* in Yeast-Cultured HDRB

Initial experiments demonstrated that *bifidobacterium* can grow in yeast-treated HDRB extract; however, it does not grow very well directly in HDRB medium. This could be due to the complex nature of the components in HDRB. HDRB was pre-treated with selected enzymes (food grade amylase containing protease, cellulase, celluclast, and viscozyme) prior to culturing with yeast and evaluated with and without pretreatments for probiotic growth. The growth performance of probiotics was similar in both the pre-treated and non-treated HDRB. Specific yeast strains contain the required enzymes that can partially degrade the complexity of rice bran. Therefore, yeast-cultured extracts are used to assess the growth performance of probiotics.

The HDRB (8 g/100 ml) in water was sterilized at 121° C. for 30 mins. After cooling to room temperature, the HDRB in water suspension was incubated with the yeast (*Saccharomyces cerevisiae* ATCC 26603/58527/7754) for 12 h. Incubation was anaerobic using GasPak at 37° C. The pH of the yeast-cultured HDRB medium dropped from 6.20 to 4.23 at 20 h incubation time. Lactic and acetic acids are produced during anaerobic fermentation.

Example 3

Anti-Microbial Activity of *Bifidobacterium*-Grown Yeast-Cultured HDRB Extract

The *Bifidobacterium* grown in sterilized yeast-cultured HDRB extract in Example 2 was evaluated for inhibition of the growth of pathogens, including *L. monocytogenes, S. typhimurium*, and *E. coli* 0157:H7. The extract was potent in inhibiting the growth of these pathogens as observed with log reductions of 5.12, 4.20, and 4.11 for *L. monocytogenes, S. typhimurium*, and *E. coli* 0157:H7, respectively, as shown in Table 1.

TABLE 1

Anti-microbial activity of *Bifidobacterium*-grown yeast-cultured HDRB extracts

| Test Organism | Control | B. adolescentis cultured HDRB extract | Reduction Log CFU/mL | B. bifidum cultured HDRB Extract | Reduction |
|---|---|---|---|---|---|
| L. monocytogenes | 9.12 | 5.00 | 4.12 | 4.00 | 5.12 |
| S. typhimurium | 9.20 | 4.70 | 4.50 | 5.00 | 4.20 |
| E. coli 0157:H7 | 9.11 | 4.48 | 4.63 | 5.00 | 4.11 |

Conditions: Extract 10 mg/ml, BHI broth culture, 37° C. for 24 h incubation, Platform shaker at 250 rpm. Source: *B. adolescentis*: ATCC 15705, *Listeria monocytogenes*: (V7 1/2a): USFDA, *B. bifidum*: ATCC 15696, *S. typhimurium*: ATCC 14028, *E. coli* 0157:H7: ATCC 43890.

Example 4

Total Phenolics and Antioxidant Activities

Phenolics were extracted and antioxidant activities were determined for rice bran, fenugreek, green tea, black tea, grape seed, ginkgo, gotu kola, fenugreek extracts. The total phenolics of the extracts, as determined by the Folin-Ciocalteau [Singleton, et al.] method, ranged from 24.8-63.5 mg of chlorogenic acid equivalent/g dry weight. Antioxidant activities determined by conjugated diene measurement of methyl linoleate were 3.4-86.3%. A higher level of antioxidant activities was observed in green tea, grape seed, and rice bran extracts (70.1%, 86.3%, and 66.0%, respectively). Although rice bran extract contained relatively less phenolics as compared to green tea and grape seed extracts, the relatively higher antioxidant activities for rice bran demonstrated that the type of phenolic constituents rather than absolute amounts are responsible for the antioxidant activities observed (Table 2).

TABLE 2

Total phenolics (mg CAE/g dw) and antioxidant activities(%) of plant extracts

| Sample Type | Total Phenolics (mg of CAE/g dw) | Antioxidant Activities (%) |
|---|---|---|
| Green tea extract | 59.8 ± 1.8$^d$ | 70.1 ± 2.4 $^c$ |
| Black tea extract | 59.3 ± 0.3 $^d$ | 52.0 ± 1.7 $^d$ |
| Grape seed extract | 63.5 ± 1.0 $^d$ | 86.3 ± 1.1 $^b$ |
| Non-cultured Rice bran extract | 39.9 ± 2.6$^f$ | 66.0 ± 0.4$^g$ |
| Ginkgo extract | 24.8 ± 1.4$^g$ | 3.4 ± 0.3$^g$ |
| Gotu kola extract | 25.4 ± 1.2 $^g$ | 3.8 ± 0.2 $^g$ |
| Fenugreek | 54.3 ± 2.6 $^e$ | 10.0 ± 0.7$^f$ |

All values of samples are on dry basis. Values are means of three determinations
Column mean values with the same letter(s) were not significantly different (p < 0.05).

An immediate objective of the present work has been to utilize heat-stabilized defatted rice bran (HDRB) as a source of growth medium for yeast, to evaluate and characterize selected components of the yeast-cultured HDRB extract (pre biotic) as potential sources of substrates for probiotics and synbiotics, and to evaluate the yeast-cultured HDRB and pro biotic grown on yeast-cultured HDRB extracts as potential sources of antioxidant and anti-mutagenic agents to improve food quality. A long-term objective is to characterize and develop practical and economical value-added applications, and functional health-promoting or disease preventing bioactives that can be consumer acceptable, shelf-stable extracts/compounds from HDRB, and/or in combination with soy meal/soy protein for synergism.

Example 5

Analysis of HDRB Extracts and Evaluation of Yeast Growth

HDRB is analyzed and quantified for selected components, including protein, starch (from broken rice), soluble and insoluble dietary fiber, total and individual phenolics and other constituents that can contribute to the growth of yeast/probiotics, and as functional bioactive compounds.

Protein content determination. Protein content of samples is determined using a Kjeldahl procedure (Kjeltec Analyzer Unit, Foss TecatorAB; Hoganas, Sweden) [AACC, 1990]. Approximately 100 mg of sample is digested with concentrated sulfuric acid in the presence of 1 Kjeltab for 1 h. The digested sample is automatically titrated using the Kjeltec Analyzer Unit with 0.1 N HCl. Kjet-Sorb is used as a receiver during titration. Protein contents are calculated using a nitrogen conversion factor of 6.25.

Starch content determination. Total starch content of samples is determined using amylo-glucosidase/a-amylase [AACC method −76.12, 1990]. Samples are weighed into a screw-capped glass tube and hydrolyzed by thermostable a-amylase and amyloglucosidase. The solution is reacted with glucose determining reagent (GOPOD containing glucose oxidase, peroxidase, and 4-aminoantipyrine) (Megazyme Intern. Ireland Ltd., Co.; Wicklow, Ireland), and the absorbance of the solution is read using a spectrophotometer at 510 nm. The readings are converted to starch content as described in the AACC method.

Soluble and insoluble dietary fiber content determination. The soluble and insoluble dietary fiber contents are determined by an enzymatic-gravimetric method following the procedure described by AACC, 1990. One gram of rice bran sample is subjected to sequential enzymatic digestion by heat-stable α-amylase, protease and amyloglucosidase. The mixture is filtered and the insoluble dietary fiber (IDF) residue washed with warm distilled water, dried and weighed. The solution of filtrate and water washings are precipitated with 4 volumes 95% ethanol for soluble dietary fiber (SDF) determination. Precipitate is filtered and dried. Both SDF and IDF residues are corrected for protein and ash content.

Total phenolic content determination. Total phenolic in the extracts is determined by the Folin-Ciocalteu method [Singleton, et al.]. Fifty milligrams of each extract is weighed into 50 ml plastic extraction tubes and vortexed with 25 mL of extraction solvent (40 mL acetone: 40 mL methanol: 20 ml, water: 0.1 mL formic acid). Then, the sample with the extraction solvent is heated (water bath) at 60° C. for 1 h, allowed to cool at room temperature, and homogenized for 30 sec. The homogenized sample is filtered into a screw-capped test tube. 1.0 mL of Folin-Ciocalteu's reagent and 1.0 mL of sodium carbonate (7.5%) is added. The tubes are vortexed, and allowed to stand for 2 h. Absorption at 726 μm is measured (Perkin-Elmer λ15 UV-vis spectrophotometer; Norwalk, Conn.). The total phenolic content is expressed as chlorogenic acid equivalents (CAE) in milligrams per gram dry material:

Total Phenolics Concentration $(FW)$ in $mg/g=(A/b)*[(SW+25)/SW]$, where A=absorbance at 726 nm; SW=sample weight (g); b=slope of standard curve of chlorogenic acid Phenolic constituents determination. The phenolics constituents are determined using HPLC by the method of Cai, et al. (2003) with some modification. One hundred milligrams of sample are extracted using 4 mL of methanol in a 65° C. water bath for 2 h. The mixture is shaken every 30 min. After extraction, the mixture is cooled to room temp and centrifuged at 10,000×g for 10 min. Three milliliters of the liquid phase are evaporated to dryness under a stream of nitrogen at 60° C. The dried extract is spiked with 0.3 mL of standard solution containing 14 known phenolic compounds and filtered through 0.2-μm filter for HPLC analysis at a flow rate of 1.0 mL/min. A TSK-GEL Super-ODS (Supelco; Bellefonte, Pa.) column is used. The mobile phases consist of solvent A (0.1% TFA in acetonitrile), solvent B (0.1% TFA in HPLC grade water) and solvent C (HPLC grade methanol, used to wash column after run). The concentrations of phenolic acids in the sample are calculated from standard curves calibrated using 14 phenolic standards and expressed in mg/100 g sample.

HDRB as a medium for yeast growth. A loop of pure cultures of Saccharomyces cerevisiae (S.c) stored at −70° C. is transferred into Potato Dextrose Broth (PDB) medium and incubated at 30° C. with shaking at 200 rpm in an incubator. Early stationary cells of yeast at 8 h cultures are inoculated at 5% (v/v) level into sterilized heat stabilized defatted rice bran (20:200 w/v water:bran), incubated for 15 h. Samples collected for 15 h at 3 h interval are plated on the Potato Dextrose Agar (PDA) plate incubated for 24 h and colonies counted. Samples collected at 3 h intervals (0, 3, 6, 9, 12, 15) are centrifuged in graduated centrifuge tubes and the amount of packed cells determined. The highest amounts of cells corresponding to the time of incubation are taken as the optimum time to produce yeast from HDRB. The incubation time (h) that gives the maximum number of CFU is taken as the optimum condition to utilize HDRB for yeast production.

Example 6

Evaluation of Yeast-Fermented HDRB Prebiotics

Yeast are cultured under controlled conditions to partially digest complex compounds in HDRB, evaluate the partially digested extract as a growth medium for beneficial intestinal organisms, including selected strains of *Bifidobacterium* and *Lactobacillus* (probiotics), and characterize selected bioactive compounds in yeast cultured HDRB extract (prebiotics) in which probiotics demonstrated optimal growth.

Controlled yeast culturing to partially digest HDRB. Yeasts are grown as described above, however, a large volume of bran:water is used. The supernatants from 0, 3, 6, 9, 12, and 15 h incubation are freeze-dried. The freeze-dried products are evaluated for the growth performance of selected strains of probiotics including *B. infantis/B. longum/B. psedolongum/B. animalis/B. bifidum/B. aldolescentis* (selected based on efficiency, viability and most commonly used in food application) and *Lactobacillus acidophilus* (one species of *Lactobacillus* selected based on the wide range of substrate utilization, and commonly used in food products). These freeze-dried extracts are also characterized for soluble and insoluble dietary fibers, oligosaccharides, total phenolics and constituents, lactic and acetic acids.

Evaluation of yeast-cultured HDRB extracts for growth performance of selected strains of *Bifidobacterium* and *Lactobacillus* (probiotics). A 10 µL-loop of pure cultures of *B. infantis/B. Longum/B. psedolongum/B. animalis/B. bifidum/B. aldolescentis/Lactobacillus acidophilus* stored at −70° C. is transferred into 10 mL of MRS broth containing (0.05% w/v) L-cysteine hydrochloride (Sigma Chemicals) (MRS-C) and incubated at 37° C. for 48 h in the anaerobic system using GasPaks. This culture (106-107 CFU/ml) is used to inoculate yeast-fermented HDRB extract medium. One hundred milliliters of each sterilized yeast cultured HDRB extract medium at varying concentration of 5/10/15 g/100 ml is used to evaluate the growth performance of *Bifidobacterium* spp. and *Lactobacillus* spp. Five percent level (5% v/v) of each *Bifidobacterium* spp. (106-107 CFU/ml) separately propagated in the standard MRS-C medium, is inoculated into each of the yeast fermented HDRB extract media (a total of 378, triplicates of *3 levels of *6 media *7 spp of *Bifidobacterium* and *Lactobacillus*) in screw-capped conical flasks, incubated anaerobically at 37° C. for 48 h using GasPak. Samples are taken every 6 h and diluted with PBS buffer (1:10 v/v, pH 7.0) and turbidity is determined at 640 nm. Noninoculated extract medium for each sample is used as the blank. Initial and final pH values of the culture media are determined. Based on the growth performance of 7 probiotics (*B. in/antis, B. Longum, B. psedolongum, B. animalis, B. bifidum, B. aldolescentis*, and *Lactobacillus acidophilus*) in 6 media at 3 concentrations, 3 probiotics, one medium and one concentration of prebiotic is selected for evaluating symbiotic activity of pre and probiotic. These selected extracts are characterized for soluble and insoluble dietary fibers, oligosaccharides, total phenolics and constituents, lactic and acetic acids.

Characterization of extracts in which the probiotics demonstrated optimal growth. The extract in which maximum growth of prebiotics was observed is characterized for selected bioactive and functional substances. It is expected that enzymes produced by yeast during fermentation under controlled conditions can release bound protein and phenolics, hydrolyze starch and fiber to oligosaccharides and organic acids, and release phenolic constituents from phenolics. Protein, starch, soluble and insoluble dietary fiber, total phenolics and phenolic constituents are characterized by procedures described above. Oligosaccharides, organic acids including lactic and acetic acids are characterized as follows:

Protein isolation. Proteins from the extracts are isolated based on a modified method adopted from Qi, et al., 1997. The extracts are dispersed in deionized water (1:10 w/v), adjusted to a pH of 8.0, stirred, and centrifuged. The supernatants are adjusted to pH 4.5, kept at 4° C. overnight to enhance protein and precipitation, and centrifuged. The proteins in the residue are solubilized at pH 7.0, and freeze dried.

Protein hydrolysis for amino acid analysis. A modified method of AOAC 982.30a (1990) is used for hydrolyzing proteins in the yeast-fermented, and probiotic-treated rice bran extracts. Ten milligrams of protein sample are hydrolyzed in 10 ml of 6.0 N HCl under vacuum at 150° C. for 12 h and evaporated under nitrogen at 60° C. Sodium diluent buffer pH 2.2 (1 mL) is added to the dried hydrolyzate, filtered and the filtrate analyzed for amino acids. Acid hydrolysis converts cysteine and methionine to cysteic acid and methionine sulfoxide/methionine sulfone, and destroys tryptophan. The extracts are pretreated with performic acid prior to hydrolysis to preserve cysteine and methionine, while alkali hydrolysis is conducted to determine tryptophan (AOAC 988. 15, 2000).

Amino acid analysis. The amino acid analysis of the filtrates is conducted on an automated amino acid analyzer (Beckman 6300, Beckman Instruments, Inc.; Palo Alto, Calif.) at a flow rate of 0.67 mL/min (0.44 mL/min for buffer solutions and 0.23 mL/min for ninhydrin solution). Sodium citrate buffers (pH 3.3, 4.3 and 6.3) are used as eluants. The amino acid contents (in g/100 g sample) are quantified by comparing them with amino acid profiles from external amino acid standard as follows: $(\text{Peak}_{sample}/\text{Peak}_{standard}) \times \text{Concentration}_{standard} \times \text{MW}_{standard}$.

Gel Electrophoresis Sample Preparation for Electrophoresis. Molecular size 14-200 kDa. Extract kept at −20° C. is removed and placed at 5° C. overnight prior to conducting SDS-PAGE electrophoresis. Samples equivalent to 2 mg protein are taken from each product, and then mixed with 0.5 mL SDS non-reducing sample buffer solution (62.5 mM Tris-HCl pH 6.8, 2% SDS, 10% glycerol, and 0.05% bromophenol blue) for SDS-PAGE electrophoresis. Two µL high molecular weight standards (14-200 kDa) are diluted with 18 µL SDS non-reducing sample buffer solution. Twelve µL of broth protein samples and standard solutions are loaded separately for each well on SDS-PAGE gel.

Molecular Size Determination:

SDS-PAGE Electrophoresis (Using high molecule weight standard) Molecular size of the proteins is determined by sodium dodecyl sulfate polyacrylamide gel electrophoresis (SDS-PAGE) according to the procedure of Laemmli. The SDS-PAGE is carried out on a slab gel (4% stacking gel, 12% of a gradient gel as separating gel) in SDS-Tris-Glycine discontinuous buffer system. Twelve micro liters, of the prepared sample solution are loaded onto the gel. Electrophoresis is performed at a constant current (60 mA per gel for approximately 45 min). The gel is stained by 0.1% Coomassie brilliant blue in acetic acid/ethanol/water solution (Oct. 40, 1950, v/v/v) and destained in the same solvent without Coomassie brilliant blue. The approximate molecular weights of extract are determined by Bio-Rad molecular weight standard ranging from 14 to 200 kDa.

Purification of oligosaccharides by ultrafiltration and nanofiltration. The high solubility and low molecular weight of oligosaccharides can be used to separate them from other components in the extract. The extract can be filtered using a Whatman paper #1 filter and centrifuged at 15,000 rpm for 10 min. The supernatant is filtered using a 0.45 µm microfilter. Higher molecular weight components in the supernatant are removed by ultrafiltration. A laboratory scale ultrafiltration unit and a 0.54 $m^2$-regenerated cellulose PREP/SCALE™-TFF-6 PLBC Cartridge (Milipore Co., Bedford, USA), with a molecular weight cut-off of 3 kDa is used. The operating conditions are maintained at 30 psi. Lower molecular weight <500 Da solutes are separated from the oligosaccharides by nanofiltration (NF90-2540 Safe water Technologies, Inc. Ill.). The operating conditions are 150 psi [Goulas, et al., 2003].

Analysis of oligosaccharides by HPLC. Purified oligosaccharides are concentrated by rotary vacuum evaporator and freeze dried. Oligosaccharides are separated and analyzed by HPLC system at 45° C. on an Animex column (Aminex HPX-42A column (300 by 78 mm; Bio-Rad, Hercules, Calif.) with water as eluent. Freeze-dried purified oligosaccharides are diluted with deionized water (10 mg/mL) and filtered through 0.45 µm-Whatman cellulose nitrate membrane filter. Sample (40 µL) is injected by an auto-sampler, and the flow rate is maintained at 0.3 ml/min. Fructo-oligosaccharides and xylo-oligosaccharides are quantified by using 1-kestose, 1,1-kestotetraose and 1,1,1-kestopentaose and xylotriose, xylotetraose and xylopentaose (Megazyme Intern. Ireland Ltd., Co.; Wicklow, Ireland), respectively as standards. Maltooligosaccharides are quantified by using maltotriose, maltotetraose, maltopentose, maltohexaose and maltoheptaose (Sigma Chemical Co.; St. Louis, Mo.) as standards. The concentrations of oligosaccharides are determined by using standard curves from the oligosaccharide standards. Peak of the HPLC chromatogram are used to identify and quantify the types of oligosaccharide.

Organic acids characterization. Organic acids (acetic and lactic acids) are determined by HPLC analysis. Acetic and lactic acid are solubilized using 10 ml of 15.8 M HNO3 and 14.9 mL of 0.009 M $H_2SO_4$ is added to 10 mg of freeze-dried extracts and centrifuged. The supernatant (2 mL aliquot) is filtered using 0.22 µm Millipore filter (Millipore Corp.; Bedford, Mass.) and analyzed for acetic and lactic acids using an Aminex HPX-87H column (300 mm×7.8 mm, Bio-Rad Laboratories; Richmond, Calif.) and a guard column with disposable cartridges H+ (Bio-Rad Laboratories) maintained at 65° C. The degassed mobile phase of 0.009 M $H_2SO_4$, filtered through a 0.45 µm membrane filter (Millipore) is used at a flow rate of 0.3 mL/min. The standard solutions of lactic and acetic acids (Sigma) are prepared in water to establish elution times, and calibration curves. The retention time for lactic acid and acetic acid is determined. The standard curve is used to identify and quantify the lactic and acetic acids [Dubey, et al, 1996].

Example 7

Development of In Vitro Synbiotic System

An in-vitro synbiotic system comprising yeast-cultured HDRB extract (prebiotic) and selected three *Bifidobacterium* spp. and *Lactobacillus* spp. (probiotics) is prepared based on the type(s) of probiotic species that demonstrated optimum growth in the partially digested HDRB by yeast described above. Shelf life stability of pro biotic and symbiotic stored at 4° C. and 10° C. is evaluated, and selected bioactive compounds produced by probiotics that demonstrated superior performance are characterized.

Evaluation of synbiotic performance of selected probiotics in model system. Selected organisms and their combination are tested for synbiotic activity in a model system. The same procedure is followed for activation and inoculation of the probiotics as described above. The anaerobic incubation is carried out at 4° C. and 10° C. temperature for 28 days. Samples (a total of 90, triplicates of *6 probiotics *1 level of prebiotic *5 time periods) per temperature are collected on weekly basis (0, 7, 14, 21, and 28 days) and evaluated for growth, viability and activity of probiotics in a symbiotic system. For evaluating growth performance, the same procedure is followed as given in the objective 2, and including calculation of specific growth rate GO, mean doubling time (Td) and pH measurements for 48 h incubation. The activity of probiotics is determined by evaluating lactic acid and acetic acid produced during 48 h incubation. The same HPLC procedure described above is used to quantify lactic and acetic acids.

Shelf life stability of probiotic and synbiotic stored at 4° C., and 10° C. The viability of the probiotics is determined on a weekly basis (0, 7, 14, 21, 28 days) by enumerating colony-forming units (CFU/ml) of probiotics. The MRS-C agar plates (MRS-C: MRS agar containing 0.05% L-cysteine hydrochloride) are used to enumerate colonies by a pour plate technique after 72 h incubation at 37° C., anaerobically. The probiotic treatment that demonstrates highest performance of growth, activity and viability is selected for evaluating synbiotic system performance.

Characterization of selected extracts in which the probiotics demonstrated optimal growth. The extract in which maximum growth of probiotics is observed is characterized for selected bioactive compounds as described above.

Example 8

Select Applications of Probiotic/Prebiotic/Synbiotic Compositions

Probiotics that demonstrate superior performance are selected and incorporated into yoghurt and beverage products. Shelf life stability is evaluated at weekly intervals of probiotics and synbiotics stored at 4° C. and 10° C. for 28 days. The concentration at which the maximum numbers of prebiotics survived/grown at 4° C. and 10° C., as well as in synbiotic combination(s) is selected for product application.

Yoghurt preparation. Industrially produced ultra high temperature (UHT) milk is used to prepare yoghurt products. One hundred milliliters of milk is heated at 85° C. for 30 min, and immediately cooled to inoculation temperature at 37° C. in an ice bath. The selected extract/inulin (prebiotic control: fructo-oligosaccharide) (Sigma) is added to the milk and cultured at 42° C. with fresh yoghurt (5% v/v) made by using commercial lyophilized yoghurt culture containing *Streptococcus thermophilus* and *Lactobacillus bulgaricus* for 4-6 h incubation. A 10 µL-loop of pure cultures of two selected probiotics based on growth performance as described, stored at −70° C. are transferred into MRS-C-L medium containing L-cysteine hydrochloride (0.05% w/v) and lactose (5% w/v) (MRS-C-L) broth and incubated at 37° C. for 48 h in the anaerobic system using GasPaks. One hundred milliliters of culture are centrifuged at 1000×g for 15 min at 4° C. and the cells are incorporated with 100 ml of yoghurt. A control is prepared without addition of prebiotics and probiotics. A total of 135 samples (triplicates of *3 prebiotics *3 probiotics *5 time periods) per temperature per type of product are inoculated and stored at 4° C./10° C. for 28 days.

Dairy beverage preparation. One hundred milliliters of reconstituted skim milk (12% w/v) are prepared by formulating non-fat dry skim milk into the deionized water. The yeast-cultures HDRB extract/inulin is added to reconstituted skim milk, and pasteurized at 70° C. for 15 min. A control is prepared without addition of prebiotics. Inoculation is preceded by the same procedure as followed in the yoghurt preparation.

Shelf life stability and evaluation 1.5 g of yoghurt/1.5 ml of reconstituted skim milk samples is evaluated for growth, activity and viability of probiotics. The same procedure is followed as described above for evaluating growth, activity and viability of probiotics in the milk products. A total of 135 samples (triplicates of *3 prebiotics*3 probiotics*5 time periods) per temperature per product is evaluated.

The sensory evaluation is conducted for a total of 9 samples (*3 prebiotic treatments: control, extract and inulin *3 pro biotic treatments: two individuals and one combined organisms) per product type on weekly basis.

Example 9

Consumer Evaluation of Probiotic/Prebiotic/Synbiotic Products

Prebiotics and synbiotics (3 total) that demonstrate superior performance in stability and growth in yoghurt and dairy beverage are selected. Sensory evaluation and consumer acceptability are conducted on products stored at 4° C. for 0, 14 and 28 days.

A nine-member trained descriptive panel is trained according to the spectrum methodology. The spectrum method involves scoring perceived intensities with reference to pre-learned scales using standard attribute names with their standards that define scale intensity [Meilgaard, et al.]. Treatments including addition of prebiotic/inulin/—into beverage or yoghurt are evaluated for appearance, aroma, flavor, and texture attributes in duplicates. Panelists undergo orientation session to establish relevant lexicon for both yoghurt and beverage. The panelists also use the orientation sessions to improve their reproducibility and accuracy. A fifteen-point intensity scale anchored by references as defined by the spectrum methodology is used in assigning values to the various descriptors. Each treatment is assessed in duplicates by all panelists on 2 consecutive days. The presentation of samples is randomized across panelists. A total of nine treatments (i.e., 3 yoghurt or beverage formulations, 2 probiotics and one synbiotic) are assessed immediately after production and after 14 and 28 days of storage at 4° C.

A two-way analysis of variance (ANOVA) is performed using statistical analysis software to determine if panelists perceived significant differences among the samples and to assess panel performance. Mean separation is performed as a follow-up analysis to determine which samples are significantly different from each other.

The consumer sample population is selected from among a database of 2,000 consumers who are 18-60 years of age and of various socioeconomic backgrounds. Consumers respond to an email survey questionnaire including demographics as well as consumption frequency of yoghurt and beverage products. Only those who consume dairy beverages or yoghurt at least twice per week are selected to participate in the assessment. With a target of 50-60 participants, a total of 70 are selected in anticipation of no shows. Respondents are provided with ID cards in the order in which they arrive at the test site and are directed to individual booths with written instructions and PDAs electronic balloting. The ID cards are assured reentrance at the next test date. A blind basis method of analysis is used, where samples are coded with randomly selected 3 digit numbers and a balanced ordered testing [Meilgaard, et al.].

Because of the rather large number of treatments (i.e., 9), the assessment is carried out over 2 days. In addition, consumer testing is performed at day 0 and day 28 of storage. Each consumer is provided with a tray with small plastic cups of beverage or yoghurt (for each 4 or 5 samples) in 50 ml plastic sample containers. To eliminate carry over factors, consumers are provided with unsalted crackers and room temperature water for mouth cleansing between samples. The consumers are asked to record their overall acceptance and acceptance of color, flavor, aftertaste, and consistency of the samples (i.e. using a 9 point hedonic scale with 9="Like extremely", and 1="dislike extremely").

Example 10

Evaluation of Anti-Oxidant Activity

Antioxidant activity determination is conducted by oxidizing linoleic acid methyl ester (MeLo) in the presence of extracts as described by Heinonen, et al. Ten milligrams of each extract is dissolved in 50 mL methanol. 0.5 mL from each methanolic extract is added to MeLo (0.2 g), and the methanol is evaporated under nitrogen. Sample aliquots (10 mg) are taken at zero time and after 72 h at 40° C. in the dark and dissolved in 5 mL of 2,2,4-trimethylpentane (isooctane), and the conjugated diene formed is measured by absorption at 234 nm using a spectrophotometer (Perkin-Elmer/λ.15 UV vis spectrophotometer; Norwalk, Conn.). The antioxidant activity is expressed as percentage (%) inhibition of formation of MeLo-conjugated diene hydroperoxides after 72 h of oxidation compared with blank from MeLo. Percentage inhibition of linoleic acid oxidation is calculated as follows: % Inhibition=$[(AB_{72\ h}-AB_{0\ h})-(AE_{72\ h}-AE_{0\ h})/(AB72_h-AB_{0\ h})]\times 100$, where A: Absorbance; E: Extract; B: Blank.

Example 11

Anti-Microbial Activity Determination

The extracts are evaluated for inhibition of *L. monocytogenes* (L.m.), *S. typhimurium* (S.t.) and *E. coli* 0157:H7 (E.c.). These extracts are tested in microbial cultures (approximately 6 logs CFU/mL) in brain heart infusion (BHI) solution and incubated for 24 h. A loop of L.m. V7 serotype (½a) FDA, S.t. and E.c., is taken from a frozen stock culture stored at −70° C. and grown in 10 mL of fresh BHI for 24 h at 37° C. in an incubator. Ten microliters of the cultures for each of the three microbials, respectively, is transferred into a 10 mL of fresh BHI and incubated for another 24 h prior to use. Twenty micro liters of each culture diluted into 10 mL of fresh BHI is used to test the antimicrobial activity of the HDRB extract. For each test, 0.5 mL of the cultures is mixed with 0.5 mL test solutions containing different levels (5-40 mg/ml) of freeze-dried HDRB extract in BHI (initial inoculum level approximately 6 logs CFU/mL). The concentration of HDRB extracts is selected based on a series of preliminary tests.

Example 13

Anti-Mutagenicity Activity Determination

The Ames test is used to test the anti-mutagenicity of extracts [Ames, et al.; Nakahara, et al.]. The following mutagens are used during the tests: B[a]P: Benzo[a]pyrene, AFB1: aflatoxin B1, Trp-P-1: 3-amino-1,4-dimethyl-5H-pyrido[4,3-b]indole from Sigma-Aldrich Chemical Co. (St. Louis, Mo.), IQ: 2-amino-3-methylimidazole[4,5-f]quinoline; Glu-P-1: 2-amino-6-methyldipyrido[1,2-a:3',2'-d]imidazole from Waka Pure Chemical Co. (Tokyo, Japan). *Salmonella typhimurium* strains TA98 and TAI 00 (indicator organism) are used for the Ames tests [Maron, et al.; Yen, et al.]. The mutagens and levels are used as follows: IQ (0.1 µg/plate for TA98 and 0.5 µg/plate for TA100), B[a]P (10 µg/plate for TA98 and 5 µg/plate for TA100), AFB1 (0.5 µg/plate for TA98 and TA100), Trp-P-1 (0.025 µg/plate for TA98 and 0.5 µg/plate for TA100), and Glu-P-1 (0.5 µg/plate for TA98 and 2 µg/plate for TA100). Extracts (0.7 mg/plate) are added to overnight cultured *S. typhimurium* TA98 or TA100 (0.1 mL), mutagen (0.1 mL) and S9 mix (0.5 mL). The entire mixture is pre-incubated at 37° C. for 20 min before molten top agar (2 mL) is added. The mixture is poured onto a minimal agar plate. The his+ revertant colonies are counted after incubated at 37° C. for 48 h [Ames, et al.]. Each sample is assayed using triplicate plates. Percentage inhibition of mutagenesis is calculated using the following equation: Inhibition (%)=[1−(number of revertants in the presence of extracts/number of revertants in the absence of extracts)]*100% [Yen, et al.].

The invention has been described hereinabove with reference to particular examples for purposes of clarity and understanding rather than by way of limitation. It should be appreciated that certain improvements and modifications can be practiced within the scope of the appended claims.

The invention claimed is:

1. A process for obtaining a yeast-rice bran ferment extract, said process comprising the steps of:
   a) grinding heat-stabilized defatted rice bran to particles;
   b) combining the particles with water to form a liquid suspension;
   c) autoclaving the liquid suspension;
   d) fermenting the liquid suspension for at least twelve hours in a medium comprising 5% w/v *Saccharomyces* yeast;
   e) centrifuging the fermented liquid suspension, thereby separating a supernatant layer, wherein the supernatant layer is the yeast-rice bran ferment extract and comprises protein, phenolic compounds, oligosaccharides, and/or arabinose released from said heat-stabilized defatted rice bran.

2. The process of claim 1, wherein the yeast-comprising medium further comprises a legume or cereal component.

3. The process of claim 2, wherein said legume component is soy meal or soy protein isolate.

4. The process of claim 1, wherein said fermenting is for a period of time less than twenty hours.

5. The process of claim 4, wherein said fermenting comprises maintaining a temperature between 30° C. and 37° C.

6. The process of claim 1, wherein said fermenting comprises maintaining a temperature between 30° C. and 37° C.

7. The process of claim 1, wherein the yeast-rice bran ferment extract is a dried extract obtained by drying the centrifuge-separated supernatant layer.

8. The process of claim 1, further comprising sonicating the liquid suspension.

9. The process of claim 8, wherein the separating further comprises separating an amount of insoluble residue from the supernatant layer.

10. The process of claim 9, further comprising drying the yeast-rice bran ferment extract to form a powdered extract.

11. The process of claim 1, wherein said yeast strain is a recombinant *Saccharomyces* yeast strain.

12. The process of claim 11, wherein said yeast strain is one or more *Saccharomyces* is selected from the group consisting of *Saccharomyces cerevisiae, Saccharomyces boulardi*, or *Saccharomyces fibuligera*.

13. The process of claim 1, wherein said *Saccharomyces* yeast is one or more yeast strain selected from the group consisting of *S. cerevisiae* ATCC 26603, *S. cerevisiae* ATCC 58527, *S. cerevisiae* ATCC 7754, *S. fibuligera* ATCC 9947, *S. cerevisiae* ATCC 13007, *S. cerevisiae* YPB-G, *S. cerevisiae* ATCC 4126, *S. cerevisiae* YPG/AB, *S. cerevisiae* YPG/MM, and *S. cerevisiae* ATCC 201160.

* * * * *